US009696218B2

(12) United States Patent
Lemmer et al.

(10) Patent No.: US 9,696,218 B2
(45) Date of Patent: Jul. 4, 2017

(54) TEST SPECIMEN HOLDER FOR HIGH TEMPERATURE ENVIRONMENTS (71) Applicant: MTS Systems Corporation, Eden Prairie, MN (US)

(72) Inventors: Steven R. Lemmer, Norwood, MN (US); Kevin Patrick McQuillan, St. Paul, MN (US)

(73) Assignee: MTS SYSTEMS CORPORATION, Eden Prairie, MN (US)

( * ) Notice: Subject to any disclaimer, the term of this patent is extended or adjusted under 35 U.S.C. 154(b) by 256 days.

(21) Appl. No.: 13/840,760

(22) Filed: Mar. 15, 2013

(65) Prior Publication Data
US 2014/0123773 A1    May 8, 2014

Related U.S. Application Data (60) Provisional application No. 61/681,127, filed on Aug. 8, 2012.

(51) Int. Cl.
G01K 13/12 (2006.01)
G01N 3/04 (2006.01)
(52) U.S. Cl.
CPC ............ *G01K 13/12* (2013.01); *G01N 3/04* (2013.01); *G01N 2203/0222* (2013.01); *G01N 2203/0226* (2013.01); *G01N 2203/0268* (2013.01)
(58) Field of Classification Search
CPC ...... G01N 3/18; G01N 2203/0222–2203/0228
USPC ............. 73/863.01, 864.91, 856–890, 766; 374/10–12, 29–39, 46–50
See application file for complete search history.

(56) References Cited

U.S. PATENT DOCUMENTS

| | | | |
|---|---|---|---|
| 3,611,787 A | 10/1971 | D'Annessa | |
| 3,795,134 A * | 3/1974 | Eichenbrenner et al. | 374/50 |
| 4,194,402 A | 3/1980 | De Nicola | |
| 4,721,000 A | 1/1988 | Scanlon | |
| 4,909,085 A | 3/1990 | Hardy | |
| 5,054,324 A | 10/1991 | Pohl | |
| 5,095,757 A * | 3/1992 | Larsen et al. | 73/857 |
| 5,119,681 A | 6/1992 | Miszczak | |
| 5,237,876 A | 8/1993 | Liu | |
| 5,269,181 A * | 12/1993 | Gibson et al. | 73/160 |
| 5,286,108 A | 2/1994 | Whatley et al. | |

(Continued)

FOREIGN PATENT DOCUMENTS

CN 201166627 Y 12/1993
CN 1412727 A 4/2003

(Continued)

OTHER PUBLICATIONS

Office Action for related Chinese patent application No. 201300523169 dated Mar. 2. 2016.

(Continued)

*Primary Examiner* — Daniel S Larkin
*Assistant Examiner* — Anthony W Megna Fuentes
(74) *Attorney, Agent, or Firm* — Steven M. Koehler; Westman, Champlin & Koehler, P.A.

(57) ABSTRACT

A test specimen holder includes a specimen engaging portion operable to selectively engage and hold a test specimen. The test specimen holder includes a first shield disposed around the specimen engaging portion wherein a first gap is formed between the shield and the specimen engaging portion to remove heat from the specimen engaging portion.

22 Claims, 9 Drawing Sheets

(56) References Cited

U.S. PATENT DOCUMENTS

| | | | |
|---|---|---|---|
| 5,329,820 | A | 7/1994 | McMahon |
| 5,481,923 | A | 1/1996 | Ohmi |
| 5,505,095 | A | 4/1996 | Raymond |
| 5,581,040 | A | 12/1996 | Lin |
| 5,945,607 | A * | 8/1999 | Peppel et al. .................. 73/856 |
| 7,568,397 | B2 | 8/2009 | Merendino, Sr. |
| 7,739,919 | B2 | 6/2010 | Sikkila |

FOREIGN PATENT DOCUMENTS

| | | | |
|---|---|---|---|
| CN | 1987408 A | 6/2007 | |
| CN | 101305273 A | 11/2008 | |
| CN | 101526451 A | 9/2009 | |
| CN | 101614640 A | 12/2009 | |
| CN | 201732028 U | 2/2011 | |
| DE | 1920767 | 11/1970 | |
| DE | 4101321 A1 | 7/1992 | |
| EP | 0573952 | 2/1994 | |
| FR | 2378273 | 3/1980 | |
| GB | 1547552 | 6/1979 | |
| JP | 60154138 A | 8/1985 | |
| JP | H102847 A | 1/1998 | |
| JP | 2009-294136 A | 12/2009 | |
| SU | 538274 A1 | 12/1976 | |
| SU | 9388088 A1 | 6/1982 | |
| WO | 9857142 | 12/1998 | |
| WO | WO 9857142 A1 * | 12/1998 | ............... G01N 3/04 |

OTHER PUBLICATIONS

PCT Search Report and Written Opinion of corresponding foreign application PCT/US2013/053696 filed Aug. 6, 2013, mailed Jan. 3, 2014.

PCT Search Report and Written Opinion of corresponding foreign application PCT/US2013/053696 filed Aug. 6, 2013, mailed Apr. 3, 2014.

MTS Systems Corporation, Grip Set Assy-680.018-OX, at least as early as Aug. 7, 2012.

MTS Systems Corporation, 646.10B Special—680 Style Collet Assy., at least as early as Aug. 7, 2012.

MTS Systems Corporation, Collet/Mandril Assy. 546.10 12 MM Air Cooled, at least as early as Aug. 7, 2012.

MTS Systems Corporation, Grip Assembly 646.10B, at least as early as Aug. 7, 2012 (2 sheets).

MTS Systems Corporation, Loadunit Accessories—311.215 40809, at least as early as Aug. 7, 2012.

MTS Systems Corporation, 646.10 Extension Assembly—High Temp, with Insulation, at least as early as Aug. 7, 2012.

Second Office Action, including Search Report, for corresponding Chinese Patent Application No. 201380052316.9, dated Oct. 18, 2016, 22 pages.

Patent Examination Report No. 1 for Australian patent application No. 2013299872, dated Aug. 22, 2016.

Chinese Office Action from the State Intellectual Property Office of People's Republic of China for Chinese patent application No. 201380052316.9, dated Apr. 13, 2017.

* cited by examiner

TEST SPECIMEN HOLDER FOR HIGH TEMPERATURE ENVIRONMENTS

BACKGROUND

The discussion below is merely provided for general background information and is not intended to be used as an aid in determining the scope of the claimed subject matter.

The present invention relates to test specimen holders, which can be used in environmental chambers. The environmental chambers can be manipulated to change the environment of a test specimen to be different from that of ambient conditions. U.S. Provisional Patent Application Ser. No. 61/681,127 filed on Aug. 8, 2012 is incorporated by reference herein in its entirety.

SUMMARY

This Summary and the Abstract herein are provided to introduce a selection of concepts in a simplified form that are further described below in the Detailed Description. This Summary and the Abstract are not intended to identify key features or essential features of the claimed subject matter, nor are they intended to be used as an aid in determining the scope of the claimed subject matter. The claimed subject matter is not limited to implementations that solve any or all disadvantages noted in the Background.

An aspect of the present disclosure includes a test specimen holder capable of withstanding high temperatures in a testing environment. The test specimen holder includes a specimen engaging portion operable to selectively engage and hold a test specimen. The test specimen holder includes a first shield disposed around the specimen engaging portion wherein a first gap is formed between the shield and the specimen engaging portion to remove heat from the specimen engaging portion Another aspect of the present disclosure includes a testing device having a base, left and right supports extending from the base, a cross head attached to the left and right supports and an actuator attached to the base. An environment chamber supported by the base and has first and second openings. A first specimen engaging portion is coupled to the actuator and configured to have a portion thereof positioned within the first opening of the environmental chamber. A second specimen engaging portion is coupled to the cross head and configured to have a portion thereof positioned within the second opening of the environmental chamber. The testing device includes a first temperature sensor proximate the first specimen engaging portion, a second temperature sensor proximate the second engaging portion and a third temperature sensor within the environmental chamber configured to sense a temperature of a specimen when retained by the first and second specimen engaging portions at a specific location. A controller is configured to receive signals from the first, second and third temperature sensors and to send a signal to control the temperatures of the first and second specimen engaging portions and configured to control a temperature of the specimen at the specific location.

DETAILED DESCRIPTION OF ILLUSTRATIVE EMBODIMENTS

Figure 1:
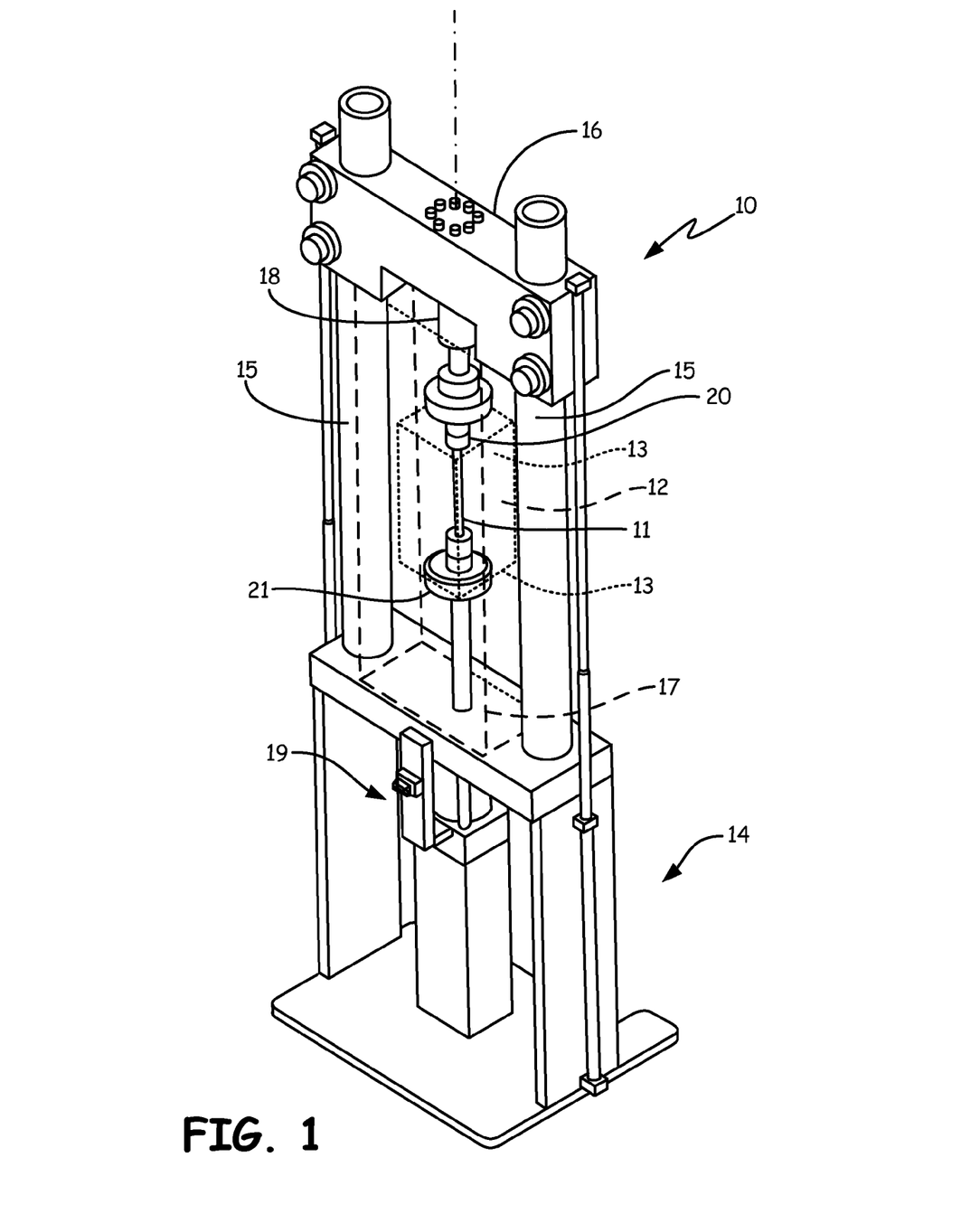
FIG. 1 is a perspective view of a testing machine with an environmental chamber.
Figure 2:
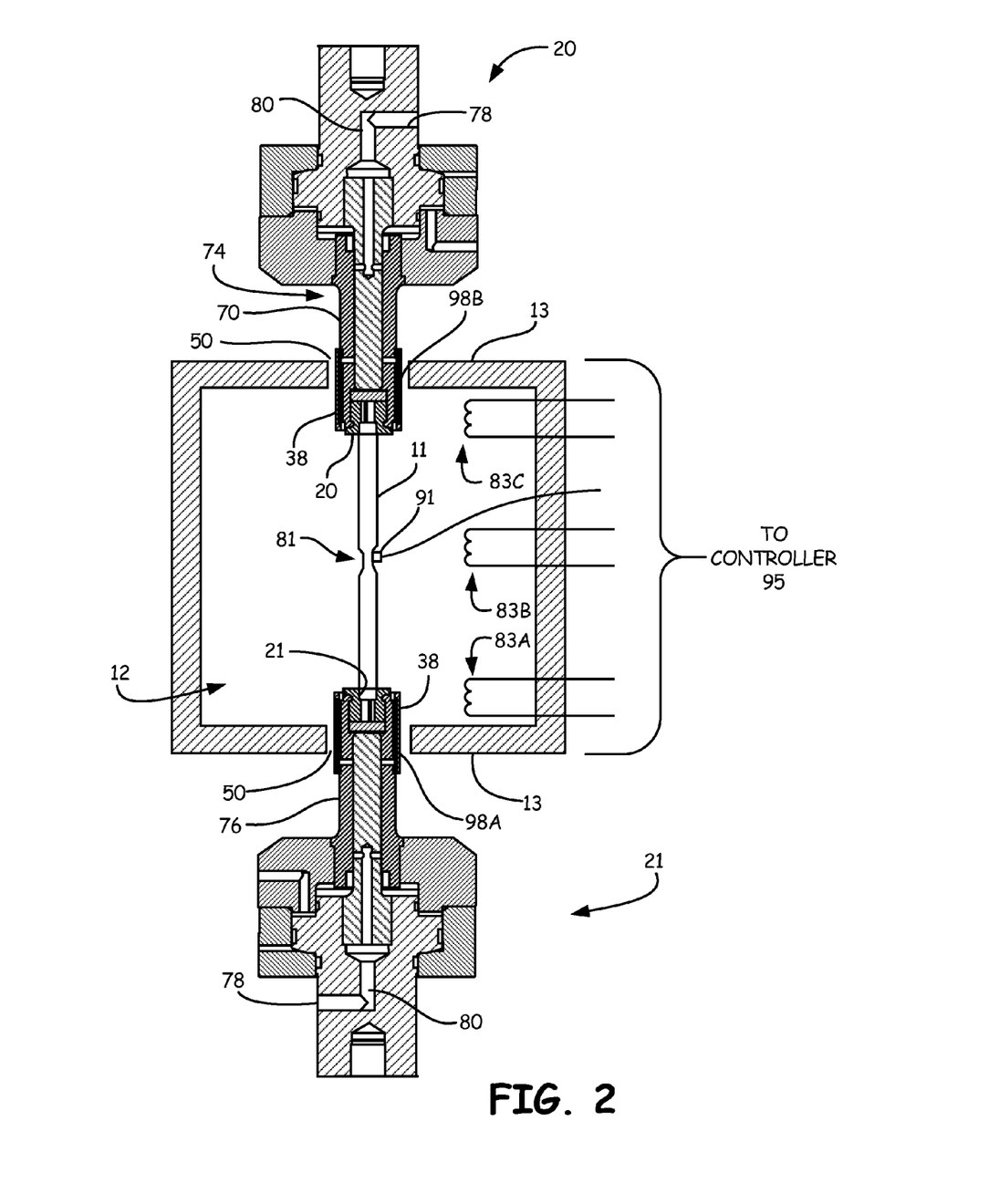
FIG. 2 is a sectional view of upper and lower test specimen holders positioned within an environmental chamber.

A load frame indicated generally at 10 in FIG. 1 is shown schematically and is used for loading a test specimen also shown schematically at 11. The specimen 11 is located in the interior of an environmental chamber 12 forming an enclosure with a pair of end walls 13 (FIG. 2). The chamber 12 can be disposed within another enclosure 17. The chamber 12 is supported relative to the load frame 10 in any desired manner, the details of which are not pertinent to the present invention disclosure. As illustrated, the load frame 10 has a base 14, a pair of upright columns 15 and a cross head 16. The cross head 16 supports a test specimen holder 20 having aspects of the present disclosure. A similar, if not identical, test specimen holder 21 is illustrated at a lower end of the environmental chamber 12. In the embodiment illustrated, the test specimen holder 21 is coupled to an actuator (indicated schematically at 19) that is located in the base 14 to apply loads or displacements. Such actuators are well known, the details of which are not pertinent to the present disclosure. A load cell 18 is often provided to measure applied loads.

At this point, it should be noted aspects of the present disclosure are not limited to the load frame 10 of the exemplary embodiment, nor are aspects of the present disclosure limited to only applying loads to the test specimen 11, although aspects of the present disclosure are particularly advantageous when loads are applied since such loads are applied through the test specimen holders 20 and 21.

Environmental chambers are commonly used to subject the test specimen 11 to high temperature environments in order to obtain measurements indicative of properties of the test specimen 11. Since at least portions of the test specimen holders 20 and 21 are also subjected to the same or similar environment as the test specimen, the test specimen holders 20 and 21 must perform satisfactory when subjected to the high temperature environment. In the case of load frames such as load frame 10, the test specimen holders 20, 21 transmit or impart loads to the test specimen 11; and therefore, they must impart these loads when the holders 20, 21 are also operating in the high temperature environment. In some cases, a user may want to perform a test at a temperature that exceeds the operating temperature of the test specimen holders 20 and/or, 21, of the operating temperature being defined by the materials upon which they are made from.

An aspect of the present disclosure provides test specimen holders 20, 21 that can be used to hold a test specimen 11 when it is desired to subject the test specimen 11 and at least portions of the test specimen holders 20 and/or 21 to a temperature that would otherwise not be practical, or even possible, given the material that the portion of the test specimen holders 20, 21 are made from.

Figure 3:
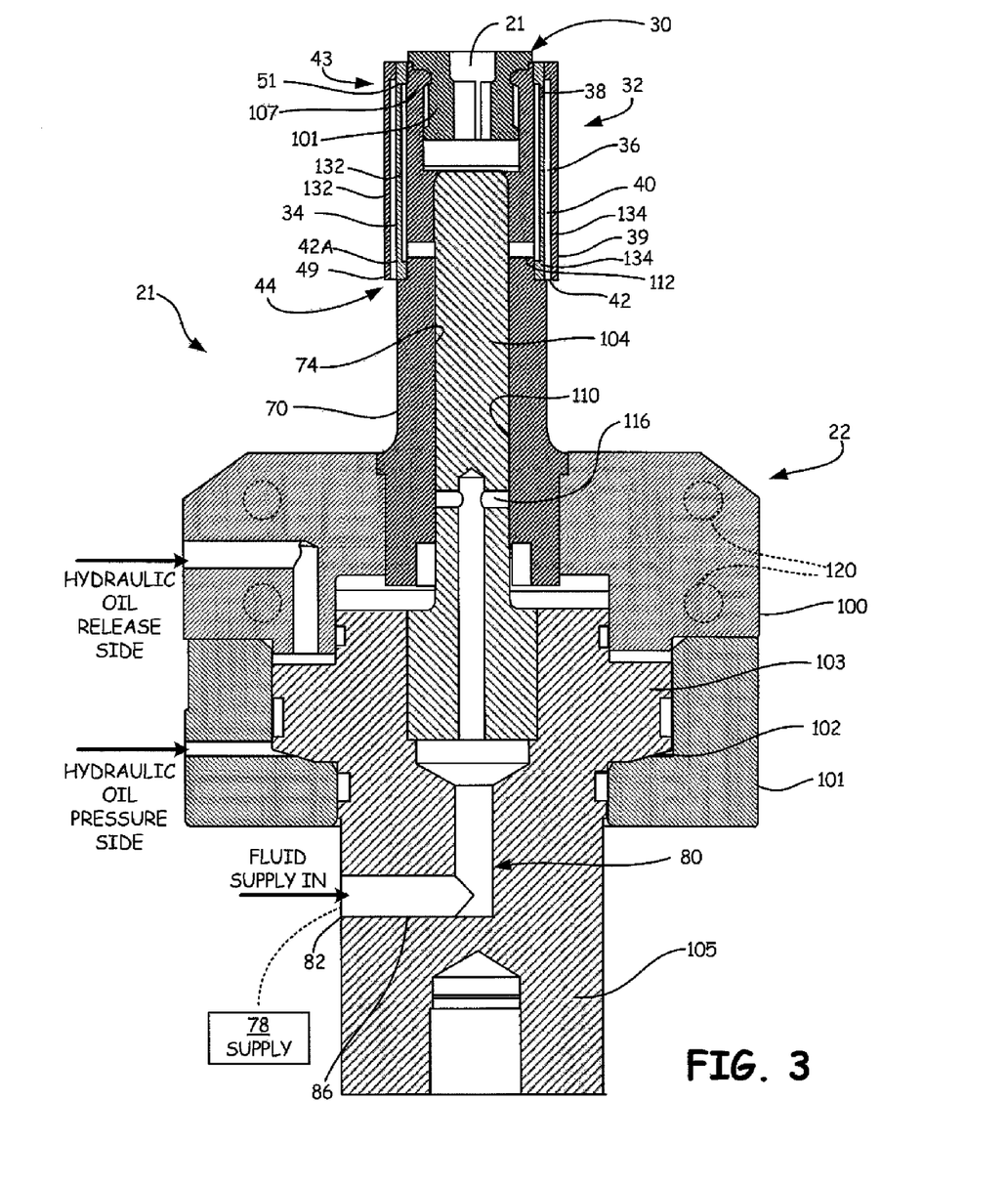
FIG. 3 is a sectional view of a test specimen holder.

Referring to test specimen holder 21 illustrated in FIG. 3 by way of example, the holder 21 includes a specimen engaging portion 30 that is configured to selectively engage the test specimen 11. A temperature modifying structure 32 is coupled to and/or is formed part of the specimen engaging portion 30. The temperature modifying structure 32 can include one or more of the features described hereinafter.

One aspect of the temperature modifying structure 32 can include one or more shields 34 disposed at least proximate to at least a part of specimen engaging portion 30. In the embodiment illustrated, the shield 34 is coupled to the specimen engaging portion 32. The shield 34 can be disposed at least proximate the specimen engaging portion 30 so as to form a cavity or gap 36 herein, by way of example an annular cavity about the specimen engaging portion 30 formed between an inwardly facing surface of the shield 34 and an outwardly facing surface of the specimen engaging portion 30 (herein extension 70).

In the embodiment illustrated, the shield 34 is fixedly attached to the specimen engaging portion 30. A gap passageway 38 can be provided to allow fluid flow out of the gap or cavity 36. In the embodiment illustrated, the gap passageway 38 comprises one or more ports provided through the material of the shield 34. If a plurality of gap passageways 38 are provided, typically, such passageways 38 are disposed in the shield 34 at angular intervals about the specimen engaging portion 30.

In the embodiment illustrated, a second shield 39 is provided and is also at least disposed proximate to a part of the specimen engaging portion 30, herein, being fixedly attached thereto by way of example by being coupled to shield 34. Preferably, a second gap or cavity 40 is formed between surfaces of the shields 34 and 39. Herein, the second cavity or gap 40 is also annular with respect to the specimen engaging portion 30. A second gap passageway 42 allows fluid flow out of the second gap or cavity 40. In this example, the second gap passageway 42 comprises a continuous annular opening about the specimen engaging portion 30 formed from the fact that the second shield 39 is coupled to the first shield 34 only at one end 43 proximate to the test specimen 11.

In FIG. 3, an alternative to the open gap passageway 42 is illustrated at 42A. A cavity 42A is created by sealing the ends 49 and 51 and pulling a vacuum on the space which removes the air from the cavity 42. The cavity 42 under vacuum contains no, or substantially no, matter, and therefore is a barrier to the passage of heat. It is also contemplated to fill the cavity with a gas, such as argon, that does not readily transfer heat. It is contemplated that the sealed cavity 42A could be used in conjunction with the gap passageways 38 and/or 42 or as a replacement for some or all gap passageway 38 and/or 42.

In the embodiment illustrated, the shield 34 engages or otherwise is held closely proximate to the specimen engaging portion 30 at an end 44 remote from the test specimen 11 and end 43. This construction is provided so as to cause most if not all of fluid flow through the gap passageway(s) 38.

However, it should be noted that an annular opening similar to gap passageway 42 can be provided between the shield 34 and the specimen engaging member 30 in addition, or in the alternative, to the gap passageway 38 herein illustrated. For instance, a gap passageway comprising an annular opening between shield 34 and the specimen engaging portion 30 in a manner similar to gap passageway 42 may be desired when only a single shield 34 is being used.

Use of passageways, such as the annular opening 42, is particularly advantageous for this structure and causes fluid flow out of the cavity connected thereto to be directed away from the test specimen 11. It should be understood that the annular opening 42 located at the end or proximate to the end of the shield 34 and/or 39 is not limited to a continuous annular opening, but rather, can be one or more port openings if one or more portions of the shield at end 44 remote from the test specimen 11 are coupled to the specimen engaging portion 30 directly or through another shield.

At this point it should be noted the specimen engaging portion 30 is disposed within the environmental chamber 12, while a portion thereof or another portion of the test specimen holder 21, extends through an opening 50 provided in the wall 13 of the environmental chamber 12 as illustrated in FIGS. 2 and 3. In a particularly advantageous embodiment, one or more of the gap passageways 38, 42 (if more than one shield is provided) is disposed so as to cause fluid flow to be directed at the opening 50 or otherwise cause fluid flow through the opening 50. In the embodiment illustrated, the wall 13 of the chamber 12 is disposed about the shield 39 so that fluid flow out of the gap passageway 42 is external to the interior of the chamber 12 where the test specimen 11 is located.

Another aspect of the present invention includes causing fluid to flow from the gap or cavity 36 and/or 40 out through the corresponding gap passageway where the fluid is expelled into the environment surrounding the test specimen holder 21. In a particularly advantageous embodiment, fluid is provided to the gap(s) or cavity (cavities) 36 and/or 40 through an internal passageway 74 provided in the specimen engaging portion 30 or a portion of the test specimen holder 21 connected thereto.

The test specimen holder 21 includes an extension 70 that extends from a base portion 72 of the test specimen holder 21, commonly located outside of the chamber 12. The extension 70 supports the test specimen engagement portion 30 on the base 72. As illustrated in FIG. 2, the extension 70 can extend through the opening 50 provided in the chamber 12. Cavity 36 is fluidly coupled to an internal passage 74 of the extension 70.

The internal passageway 74 also extends through the opening 50 and is fluidly coupled to a fluid supply source 78. The fluid supply source 78 can take any number of forms including a pressurized container, pump, fan, or the like. In the embodiment illustrated, the internal passageway 74 is fluidly coupled to a passageway 80 in base 72 wherein an inlet port is provided at 82.

An aspect of the disclosure includes is using fluid flowing through the internal passageways of the extension 70 and/or flowing through the gap(s) 36, 40 and/or other passageways to cool or lower the temperature of the specimen engaging portion 30 and/or extension 70 so that they can be used in environmental chambers 12 heated to a temperature in excess of what these components could otherwise operate without such measures taken given the materials that they are made of.

Referring to FIG. 2, commonly testing of a test specimen includes heating a portion (e.g. center portion 81) to a desired temperature. In many tests, a temperature gauge 91 is provided so as to monitor the temperature. In addition to achieving the desired temperature, in many cases it is also necessary that the temperature be constant over an axial length (between the holders 20, 21) of the portion 81 of the test specimen under test. In other words, it is often desired that a certain temperature gradient be obtained over the portion 81 under test, typically a very small gradient.

To control the temperature in an environmental chamber 12, the environmental chamber 12 commonly includes a plurality of heating elements to emit radiant heat energy. In one form of environment chamber 12, three heating elements 83A, 83B and 83C (schematically illustrated) are provided where a center heating element 83B is disposed proximate the test specimen 11 and in particular the portion 81 under test, while end heating elements 83A and 83C are disposed so as contribute heat at the end portions of the environmental chamber 12 proximate the ends of the test specimen holders 20, 21.

Referring to FIGS. 2 and 3, it has been found that using one or more of the temperature modifying structures 32 herein described, and in particular, fluid flow from the supply 78 through the gap(s) 36, 40 can be used to maintain the temperature of the specimen engaging portion 30 and/or extension 70 or other components of the holder 21 in the chamber 12 so as to operate (herein transfer or impart desired load), whereas the portion 81 of the test specimen 11 is heated (maintaining a desired temperature gradient) to a temperature in excess of the temperature of the specimen engaging portion 30, etc.

For example, it has been found that the portion 81 can be heated to 1200° C., while the specimen engaging portion 30, the extension 70, etc. does not exceed 1000° C. by flowing fluid through gap(s) 36, 40 and connected passageways. Typically, the fluid is a gas, for example but not limited to air, inert gases, etc. The degree or extent of the cooling provided to the specimen engaging portion 30, extension 70, etc. can be varied by varying the type fluid, the temperature of the fluid into the holder 21 and the rate at which the fluid is provided. If desired, the fluid can even be provided from the source 78 as a liquid, wherein energy is absorbed and a change in state to a gas occurs, where gas is emitted from the passageway(s) 38, 42.

Figure 8:
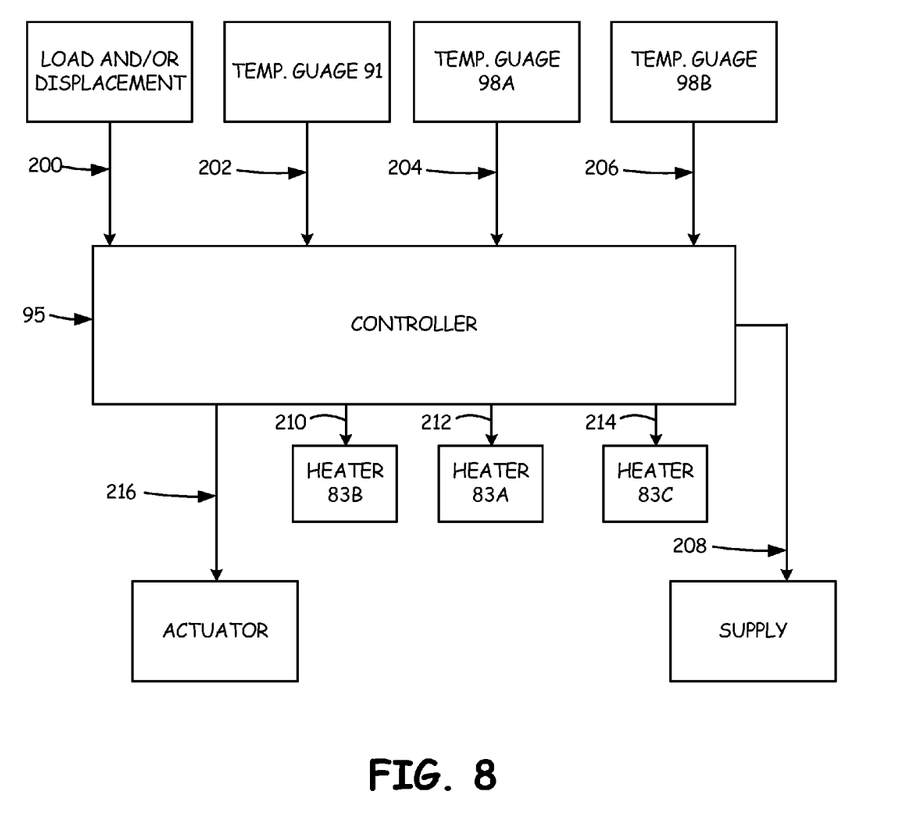
FIG. 8 is a schematic view of a control system for the testing machine.

Referring to FIG. 8, a controller 95, that is schematically illustrated, commonly is provided. The controller 95 can receive data indicative of the test specimen 11 during the test. With the load frame 10, such inputs data can include a measurement of load 200 applied to the test specimen 11 from the load cell 18 and/or a measure of displacement indicative of extension or compression of the test specimen 11 under load from an extensometer, not shown. These are but merely examples and may or may not form part of the present invention.

As indicated above, the controller 95 can also receive a first temperature input 202 from temperature gauge 91. If desired, each of the holders 20, 21 can also include temperature gauges 98A, 98B, respectively, each of which provides a temperature input 204, 206, respectively, to controller 95 indicative of the temperature of the corresponding holder 20, 21, and in one embodiment the specimen engaging portion 30 of each. Such temperature gauges are well known.

Controller 95 can be configured to provide control signals 208 to supply 78 to adjust any of the aforementioned parameters (e.g. temperature of fluid, rate of flow, pressure, etc.). In one embodiment, a user can operate a user interface of controller 95 so as to manually adjust one or more of these parameters based on any one or more of the temperature inputs received, for example, the temperatures of the specimen 11 or the holders 20, 21 at 210, 212 and 214, respectively. In a further embodiment, controller 95 can automatically adjust one or more of these parameters based on parameters based on any one or more of the temperature inputs received, for example, the temperatures of the holders 20, 21. The controller 95 also can be configured to send a signal 216 to the actuator in response to the signal 200.

Figure 4:
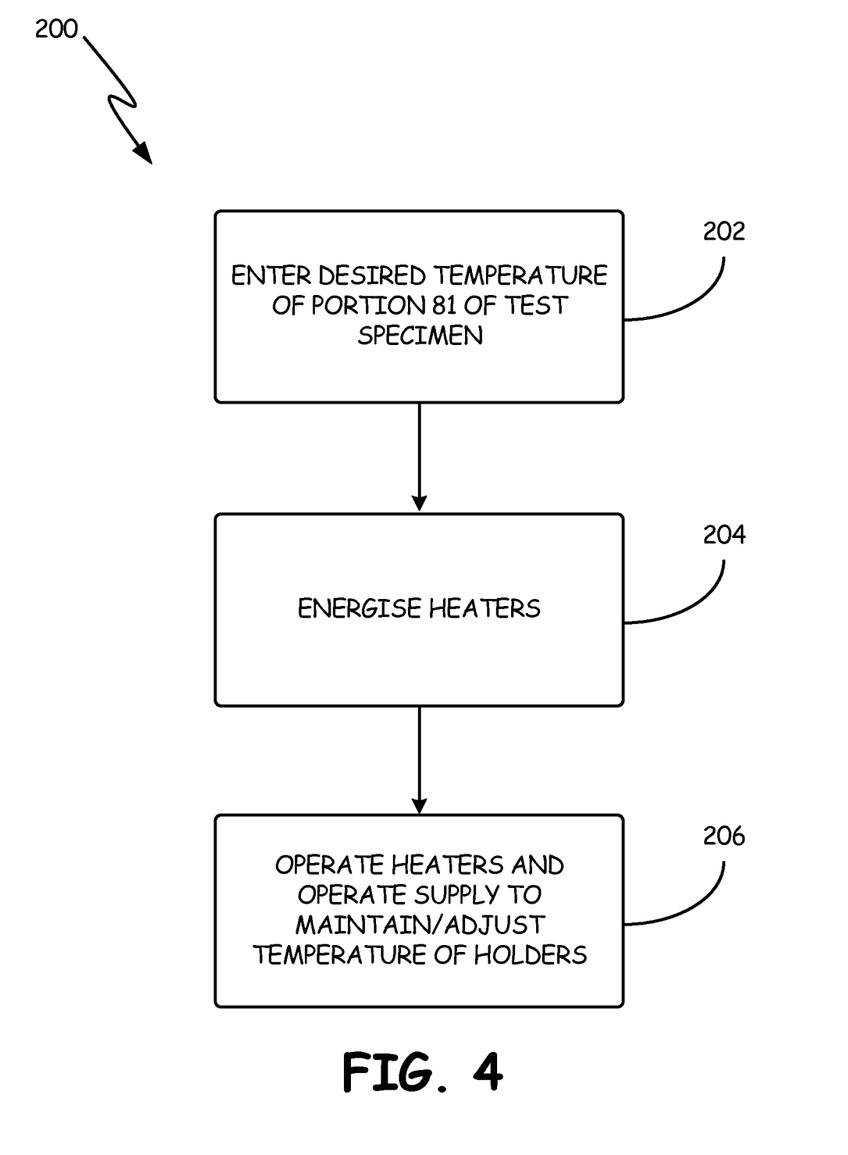
FIG. 4 is a flow diagram for controlling the environment within the environmental chamber.

FIG. 4 illustrates an exemplary method 200 for automatic adjustment of the supply 78 so as to maintain the desired temperature on each of the holders 20, 21. At step 202, the desired temperature for the test portion 81 is entered into controller 95, for example, through a suitable user interface. At step 204, the controller 95 can operate heaters 83A, 83B and 83C to obtain the desired temperature. Throughout method 200, controller 95 receives temperature signals from the aforementioned temperature gauges 91, 98A, and 98B. The controller 95 then remains in step 206 where the heaters 83A, 83B and 83C are operated, if necessary, to maintain the desired temperature of the portion 81. More importantly though, controller 95 adjusts parameters of the fluid provided to the holders 20, 21 and in particular to gap(s) 36, 40 in order to maintain the temperature of the holder 20, 21 at a desired temperature within the operating range of each holder 20, 21, which is less than the temperature of the portion 81. By controlling the parameters of the fluid provided to the holders 20, 21 the temperature of the holders 20, 21 can be precisely adjusted.

It is important to note that in a one embodiment, the controller 95 does not merely controlled the supply 78 so as to obtain any desired temperature that is less than the temperature that the holder 20, 21 should operate below. Rather, the controller 95 controls the supply 78 and/or heaters 83A, 83B and 83C so as to obtain a temperature of the holder 20, 21 that is within the desired operating range, but does not cool the specimen engaging portion 30 so as to cause an undesired temperature gradient across the portion 81 of the test specimen 11.

Referring to FIG. 3, although not required, the test specimen holder 21 comprises an actuatable assembly for selectively gripping and releasing the test specimen 11. As illustrated in the exemplary embodiment, the base 72 comprises an actuator (e.g. manually operated, hydraulic or pneumatic, etc.) that has an outer cylinder body section 100 with an actuator end cap 101 held thereon to form an internal chamber 102 in which a piston 103 and extending rod portion 104 are mounted. The piston 103 has a second rod portion 105 (which can be a separate part or integral with piston 103 being formed of a single unitary body) that extends out through an opening in the base of the cylinder body 100. Rod portion 105 is connected through suitable connections such as a threaded connection to a rod of the actuator 19 that is mounted in the base 14 of the load frame 10.

Generally, a fluid passageway 80 is provided from port 82 in base 72 to passageway 74 so as to be fluidly coupled to cavity or gap 36. In the embodiment illustrated, internal passageway 74 in extension 70 includes an inner bore 110 and lateral passageways 112 which fluidly couple the inner bore 110 with the gap or cavity 36. Rod 104 also includes internal passageways 116 that fluidly couple the inner bore 110 to the port 82.

It should be understood that this is but one embodiment, the particular structure of which however has advantages when the specimen holder 21 includes the actuator component. In particular, cylinder body 100 moves relative to piston 103 in order to cause specimen engaging portion 30 to engage or release the test specimen 11. Extension 70 is fixedly coupled or formed integral with cylinder body 100 as a single unitary body, so that extension 70 moves with cylinder body 100 relative to rod 104.

In the embodiment illustrated, specimen engaging portion 30 includes a test specimen receiver 101 that can be selectively compressed to engage the test specimen 11. Extension 70 includes an inwardly extending annular flange 107 that engages the test specimen receiver 101. The test specimen receiver 101 and annular flange 107 are configured such that displacement of the extension 70 (in FIG. 3 downwardly) compresses the test specimen receiver 101 so as to grip the test specimen 11 without imparting tension in the test specimen 11 between the holders 20 and 21. It should be understood that the test specimen receiver 101 can take other configurations.

Figure 5:
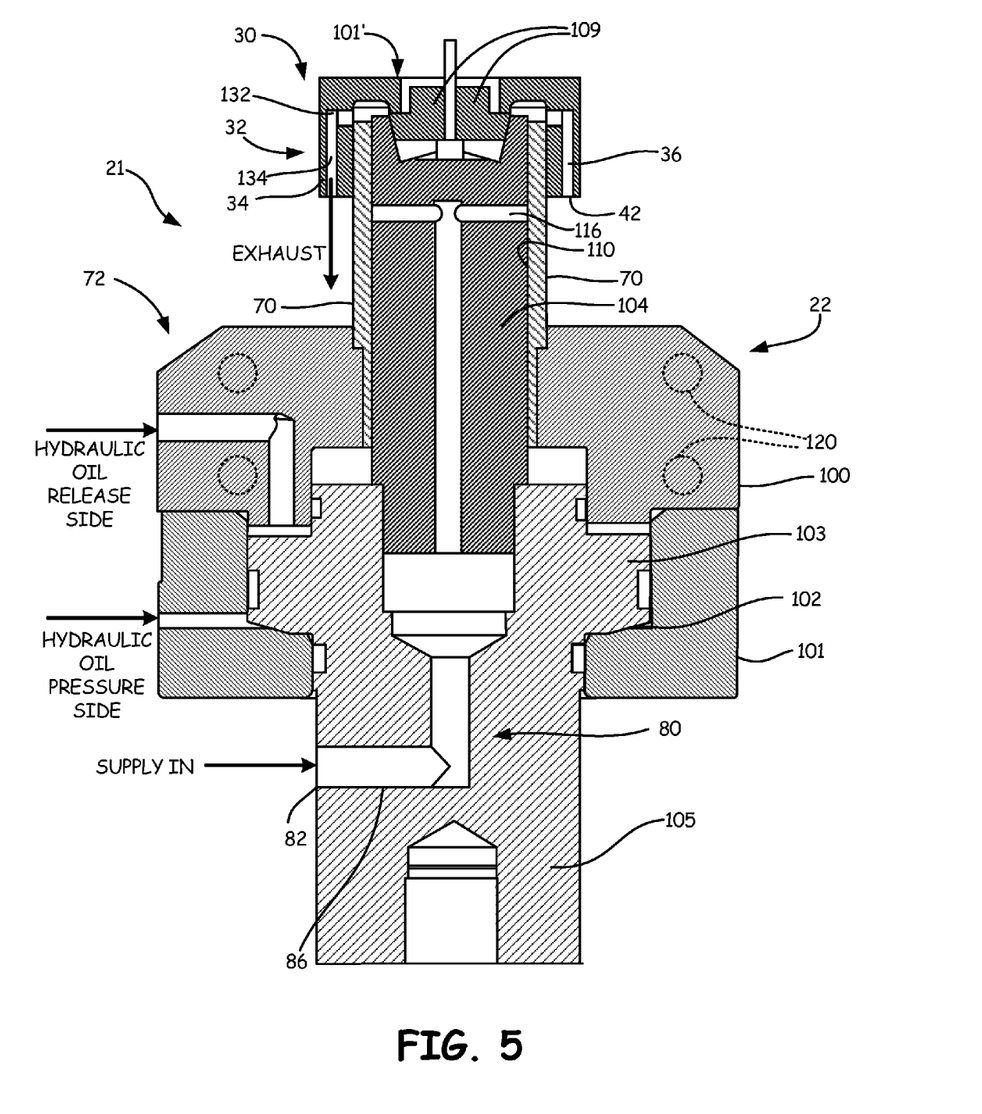
FIG. 5 is a sectional view of another embodiment of the test specimen holder.

Referring to FIGS. 3 and 5 where similar or identical parts have been identified with the same reference number, test specimen receiver 101' includes wedges 109 that move laterally toward and away from the test specimen 11 to selectively engage the test specimen 11. Again, operation of test specimen receiver 101' occurs with movement of the extension 70 and cylinder body 100 relative to rod 104. Other forms of test specimen receivers are illustrated in U.S. Pat. No. 5,095,757 as other displaceable wedges and clamping collets. These and other forms of test specimen receivers can be used with aspects of the present invention herein described and/or illustrated.

It should be noted that it is common for cooling to be provided for the base 72 of test specimen holder 21 via base cooling passageways schematically indicated at 120, which in turn are fluidly coupled to inlet and outlet ports (not shown). In a particularly advantageous embodiment, the fluid provided to cavity or gap 36 and various passageways connected thereto are separate and isolated from cooling passageways 120.

Another aspect of the present disclosure, in particular, the temperature modifying structure 32, includes one or more of the exterior surfaces of the holder 20, 21 exposed to heat in the environmental chamber 12 such as test specimen receiver 101, extension 70, shields 34, 39, and/or other components forming part of specimen engaging portion 30 comprising a material that inhibits heat absorption or heat transfer via conduction, convection and/or radiation. The material can comprise the entire component or one or more layers over a base material (metal or non-metal). A thermal barrier material such as but not limited to a ceramic inhibits the conduction or absorption of heat from the environmental chamber 12 to the specimen engaging portion 30. By way of example, any surface (e.g. outwardly facing surface 132 and/or inwardly facing surface 134 of the shields 34 and 39, outer surfaces of test specimen receiver 101 and/or extension 70) or the component in its entirety, can comprise a thermal barrier material that helps prevent the transmission of heat to the specimen engaging portion 30.

It has also been found that low emissivity thermal materials such as but not limited to thin coatings of metals or coatings having metal particles provided on or otherwise forming selected surfaces of the shields 34 and 39 also inhibits heat transfer to the specimen engaging portion 30. For instance, inwardly facing surfaces 134 of shields 34 and/or 39 can be provided with a low emissivity thermal coating so as to minimize radiant heat energy from being emitted therefrom. It should also be noted both thermal barrier materials and low emissivity thermal materials can be combined on the same component.

Figure 6:
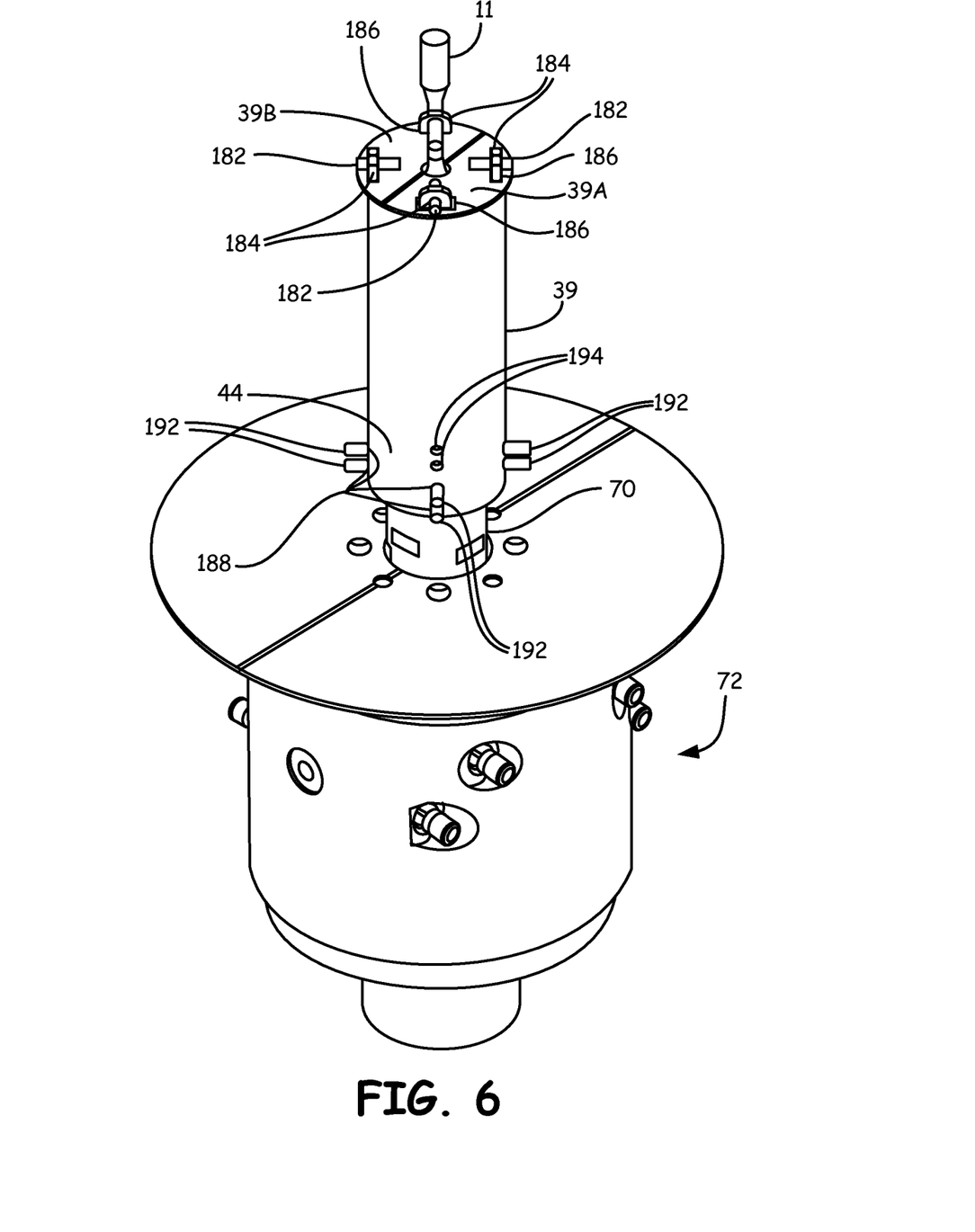
FIG. 6 is a perspective view of the test specimen holder with additional shielding.
Figure 7:
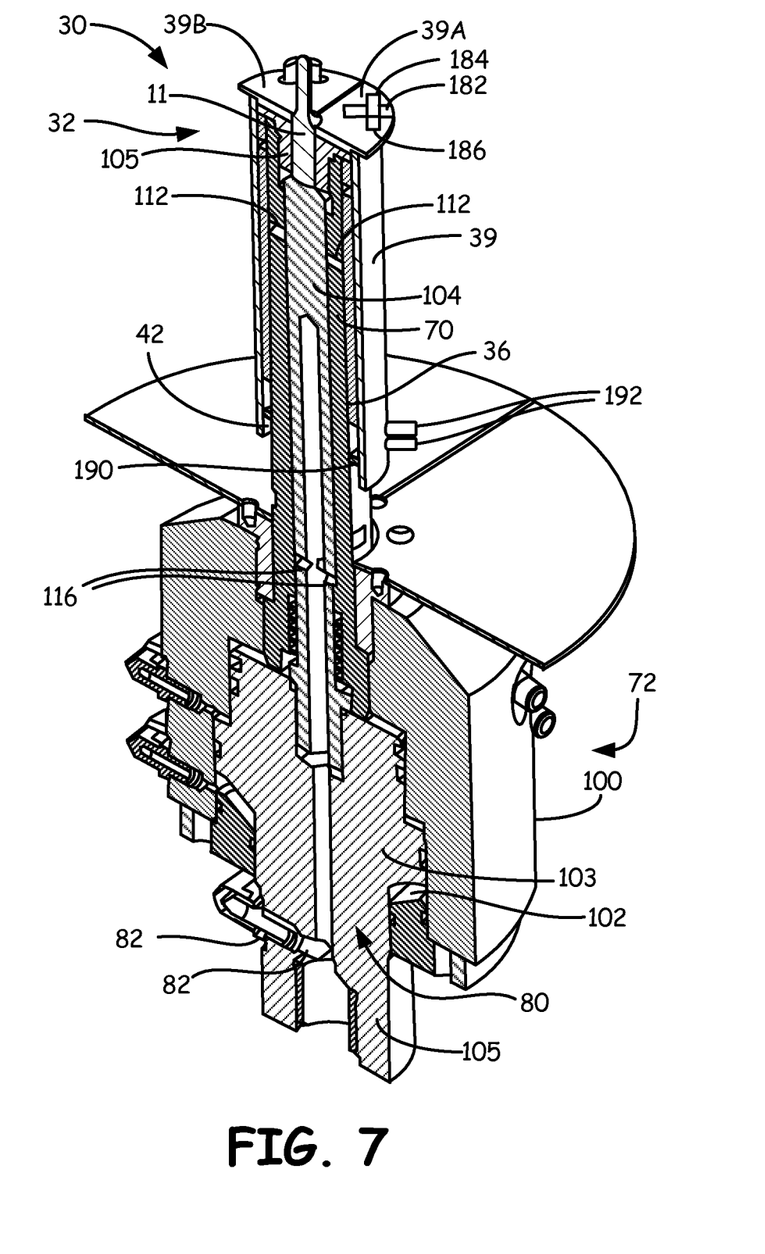
FIG. 7 is a cutaway perspective view of the test specimen of FIG. 6 taken along a vertical mid-plane.

FIGS. 6 and 7 illustrate another holder 180 having aspects of the present disclosure. Those components having similar or same functions as described above have been identified with like reference numbers. In this embodiment, shield 39 further includes top plate portions 39A and 39B that cover much if not if not all of specimen receiver 105. Plate portions 39A and 39B are secured to shield 39 using pins 182 that are inserted into apertures of upstanding flange portions 184, the flange portions 184 extending through apertures 186 in plate portions 38A, 38B.

Additional pins 192 are provided proximate an end 44 of the shield 39. When the shield 39 is disposed over the extension 70, apertures 188 are disposed on each side of an annular flange 190 on rod 104. Pins 192 (for example, made from ceramic) are inserted in the apertures 188 so as to inhibit axial movement of the shield 39 by contact with the annular flange 190. In view of the presence of annular flange 190, passageway 42 comprises vent outlets 194.

It should be noted that controller 95 is illustrated only schematically in FIG. 8, wherein functionality of this component may be implemented on one or more computing devices. For example, in one embodiment, the controller 95 can comprise a user operated terminal, system controller and a servo controller. The servo controller provides control signals to operate the actuator 19 based on commands provided from a system controller. The system controller typically receives actual responses as feedback in a response to a drive provided as input to the servo controller. The user operated terminal provides overall command signals to the system controller.

The controller 95, user operated terminal, servo controller or system controller, discussed above can each be implemented, at least in part, on a digital and/or analog computer. FIG. 8 and the related discussion provide a brief, general description of a suitable computing environment comprising a general computing device. Although not required, the general computing device will be described, at least in part, in the general context of computer-executable instructions, such as program modules, being executed by a computer 302.

Generally, program modules include routine programs, objects, components, data structures, etc., which perform particular tasks or implement particular abstract data types. Those skilled in the art can implement the description below and/or block diagrams to computer-executable instructions storable on a computer readable medium. Moreover, those skilled in the art will appreciate that the disclosure may be practiced with other computer system configurations, including multi-processor systems, networked personal computers, mini computers, main frame computers, and the like. Aspects of the disclosure may also be practiced in distributed computing environments where tasks are performed by remote processing devices that are linked through a communications network. In a distributed computer environment, program modules may be located in both local and remote memory storage devices.

Figure 9:
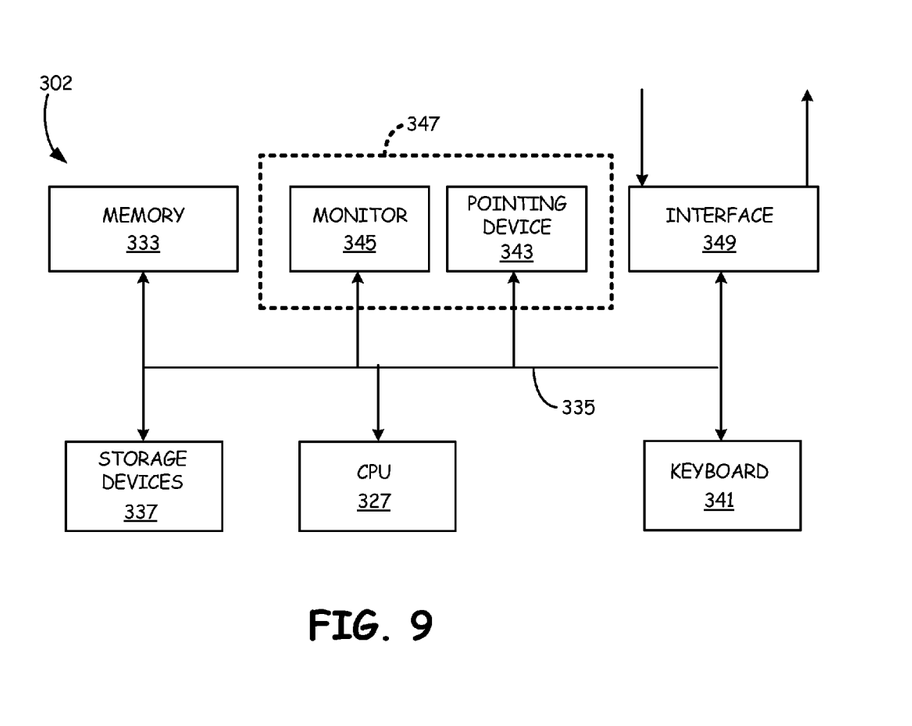
FIG. 9 is a schematic flow diagram of a computer.

The computer 302 illustrated in FIG. 9 comprises a conventional computer having a central processing unit (CPU) 327, memory 333 and a system bus 335, which couples various system components, including memory 333 to the CPU 327. System bus 335 may be any of several types of bus structures including a memory bus or a memory controller, a peripheral bus, and a local bus using any of a variety of bus architectures. The memory 333 includes read only memory (ROM) and random access memory (RAM). A basic input/output (BIOS) containing the basic routine that helps to transfer information between elements within the computer 302, such as during start-up, is stored in ROM. Storage devices 337, such as a hard disk, a floppy disk drive, an optical disk drive, etc., are coupled to the system bus 335 and are used for storage of programs and data. It should be appreciated by those skilled in the art that other types of computer readable media that are accessible by a computer, such as magnetic cassettes, flash memory cards, digital video disks, random access memories, read only memories, and the like, may also be used as storage devices. Commonly, programs are loaded into memory 333 from at least one of the storage devices 337 with or without accompanying data.

Input devices such as a keyboard 341 and pointing device (mouse) 343, or the like, allow the user to provide commands to the computer 302. A monitor 345 or other type of output device is further connected to the system bus 335 via a suitable interface and provides feedback to the user. If the monitor 345 is a touch screen, the pointing device 343 can be incorporated therewith.

Interfaces 349 on each of the controller 95, servo controller or system controller allow communication. Interface 349 also represents circuitry used to send signals or receive signals as described above. Commonly, such circuitry comprises digital-to-analog (D/A) and analog-to-digital (A/D) converters as is well known in the art. The controller 95 can also comprise an analog controller with or without digital supervision as is well known.

Although the present invention has been described with reference to preferred embodiments, workers skilled in the art will recognize that changes may be made in form and detail without departing from the spirit and scope of the invention.

What is claimed is:

1. A test specimen holder comprising:
   a specimen engaging portion operable to selectively engage and hold a test specimen; and
   a first shield fixedly attached to and disposed around the specimen engaging portion wherein a first annular gap is formed between an inwardly facing surface of the first shield and an outwardly facing surface of the specimen engaging portion to remove heat from the specimen engaging portion by exhausting fluid from the first annular gap to an outside environment.

2. The test specimen holder of claim 1 and wherein the first annular gap comprises a first gap passageway having an inlet port and an exhaust port, wherein a gas is forced into the first gap passageway through the inlet port and heat is transferred from the specimen engaging portion through the first gap passageway.

3. The test specimen of claim 2 and wherein the inlet port is at a first end of the first gap passageway and the exhaust port is at a second end of the first gap passageway.

4. The test specimen of claim 1 and further comprising a second shield attached to the specimen holder and disposed about the first shield wherein the second shield is attached to the first shield to define a second gap passageway that is configured to remove heat from the specimen holder when a gas flows therethrough.

5. The test specimen of claim 4 and wherein the second gap passageway comprises an inlet port at a first end of the second gap passageway and an exhaust port at a second end of the second gap passageway such that heat is removed from the specimen engaging portion when a gas flows therethrough.

6. The test specimen holder of claim 4 and wherein the second shield includes at least one surface comprising a thermal barrier coating or a low emissivity thermal coating.

7. The test specimen holder of claim 6 wherein the at least one surface on the second shield is an inwardly facing surface spaced apart from and facing an outwardly facing surface of the first shield, the inwardly facing surface of the second shield having the thermal barrier coating or a low emissivity thermal coating.

8. The test specimen holder of claim 1 and wherein the first shield includes at least one surface comprising a thermal barrier coating or a low emissivity thermal coating.

9. The test specimen holder of claim 8 wherein said at least one surface comprises an inwardly facing surface spaced apart from the specimen engaging portion to form a gap.

10. The test specimen holder of claim 1, wherein the specimen engaging portion comprises an internal passageway configured to provide fluid to the first annular gap.

11. The test specimen holder of claim 1, wherein the first shield is further configured to move air about and along the specimen engaging portion at an end of the specimen engaging portion.

12. A test specimen holder comprising:
   a specimen engaging portion operable to selectively engage and hold a test specimen; and
   a first shield disposed around the specimen engaging portion wherein a first gap is formed between the first shield and the specimen engaging portion to remove heat from the specimen engaging portion;
   wherein the first gap comprises a sealed cavity under a vacuum and wherein the sealed cavity under vacuum prevents heat transfer to the specimen engaging portion.

13. An apparatus for a testing device having a base, left and right supports extending from the base, a cross head attached to the left and right supports, and an actuator attached to the base, the apparatus comprising:
   an environmental chamber having first and second openings;
   a first specimen engaging portion configured to be coupled to the actuator and having a portion thereof positioned within the first opening of the environmental chamber;
   a second specimen engaging portion configured to be coupled to the cross head and having a portion thereof positioned within the second opening of the environmental chamber;
   a first temperature sensor proximate the first specimen engaging portion;
   a second temperature sensor proximate the second specimen engaging portion;
   a third temperature sensor within the environmental chamber configured to sense a temperature of a specimen at a specific location; and
   a controller configured to receive signals from the first, second and third temperature sensors and to send a signal to control the temperatures of the first and second specimen engaging portions and configured to control a temperature of the specimen at the specific location, wherein the temperature of the specimen at the specific location is greater than the temperatures of the first and second specimen engaging portions, and to induce and maintain a temperature gradient at the first and second specimen engaging portions.

14. The apparatus of claim 13 and further comprising:
   a first heating element positioned within the environmental chamber next to the first specimen engaging portion;
   a second heating element positioned within the environmental chamber next to the second specimen engaging portion; and
   a third heating element positioned within the environmental chamber and configured to control a temperature of a specimen at the specific location.

15. The apparatus of claim 14 and wherein the controller individually controls the first, second and third heating elements from signals from the first, second and third temperature sensors such that the first and second heating elements are controlled to a selected temperature and the third heating element is configured to control the temperature of a specimen at a selected location.

16. The apparatus of claim 13 and wherein the first and second specimen engaging portions both comprise:
   a specimen engaging portion operable to selectively engage and hold a test specimen; and
   a first shield disposed around the specimen engaging portion wherein a first annular gap is formed between an inwardly facing surface of the first shield and an outwardly facing surface of the specimen engaging portion to remove heat from the specimen engaging portion, the first shield configured to move air about and along the specimen engaging portion at an end of the specimen engaging portion.

17. The apparatus of claim 16 and wherein each first annular gap comprises a first gap passageway having an inlet port and an exhaust port, wherein a gas is forced into the first gap passageway through the inlet port and heat is transferred heat from each corresponding specimen engaging portion.

18. The apparatus of claim 16 and further comprising a second shield attached to each of the specimen engaging portions and disposed about each corresponding first shield wherein each second shield is attached to each corresponding first shield to define a second gap passageway that is configured to remove heat from the specimen engaging portions by flowing gas from an inlet port and through the second gap passageway and exhausted through an outlet port.

19. The apparatus of claim 18 and wherein the second shield of both the first and second specimen engaging portions includes at least one surface comprising a thermal barrier coating or a low emissivity thermal coating.

20. The apparatus of claim 16 and wherein the first annular gap of both the first and second specimen engaging portions comprises a sealed cavity under a vacuum wherein the sealed cavity under vacuum prevents heat transfer to the specimen engaging portion.

21. The apparatus of claim 16 and wherein the first shield of both the first and second specimen engaging portions includes at least one surface comprising a thermal barrier coating or a low emissivity thermal coating.

22. The apparatus of claim 21 wherein said at least one surface comprises an inwardly facing surface spaced apart from the specimen engaging portion to form a gap.

* * * * *